US010232079B2

(12) United States Patent
Grunwald et al.

(10) Patent No.: US 10,232,079 B2
(45) Date of Patent: Mar. 19, 2019

(54) GEL-FORMING SYSTEM FOR REMOVING URINARY CALCULI AND FRAGMENTS THEREOF

(71) Applicants: FRAUNHOFER-GESELLSCHAFT ZUR FÖDERUNG DER ANGEWANDTEN FORSCHUNG E.V., München (DE); ALBERT-LUDWIGS-UNIVERSITÄT FREIBURG, Freiburg (DE)

(72) Inventors: Ingo Grunwald, Lilienthal (DE); Katharina Richter, Bremen (DE); Arkadiusz Miernik, Freiburg (DE); Martin Schoenthaler, Freiburg (DE)

(73) Assignees: FRAUNHOFER-GESELLSCHAFT ZUR FÖRDERUNG DER ANGEWANDTEN FORSCHUNG E.V., Munich (DE); ALBERT-LUDWIGS-UNIVERITÄT FREIBURG, Freiburg (DE)

( * ) Notice: Subject to any disclaimer, the term of this patent is extended or adjusted under 35 U.S.C. 154(b) by 0 days.

(21) Appl. No.: 14/786,810

(22) PCT Filed: Aug. 22, 2013

(86) PCT No.: PCT/EP2013/067434
§ 371 (c)(1),
(2) Date: Oct. 23, 2015

(87) PCT Pub. No.: WO2014/173467
PCT Pub. Date: Oct. 30, 2014

(65) Prior Publication Data
US 2016/0067373 A1    Mar. 10, 2016

(30) Foreign Application Priority Data

Apr. 23, 2013   (EP) .................................... 13164955

(51) Int. Cl.
| | |
|---|---|
| *A61L 24/08* | (2006.01) |
| *A61L 24/00* | (2006.01) |
| *A61L 24/04* | (2006.01) |
| *A61L 24/02* | (2006.01) |
| *A61B 17/22* | (2006.01) |
| *A61B 17/00* | (2006.01) |

(52) U.S. Cl.
CPC .......... *A61L 24/08* (2013.01); *A61L 24/0031* (2013.01); *A61L 24/02* (2013.01); *A61L 24/04* (2013.01); *A61B 17/22* (2013.01); *A61B 2017/00876* (2013.01); *A61B 2017/22082* (2013.01); *A61L 2430/26* (2013.01)

(58) Field of Classification Search
None
See application file for complete search history.

(56) References Cited

U.S. PATENT DOCUMENTS

| | | |
|---|---|---|
| 5,244,913 A | 9/1993 | Coulter et al. |
| 6,544,227 B2 | 4/2003 | Sahatjian et al. |
| 6,663,594 B2 | 12/2003 | Sahatjian et al. |
| 2002/0119116 A1 | 8/2002 | Sahatjian et al. |
| 2003/0100752 A1 | 5/2003 | Robinson |
| 2006/0074409 A1* | 4/2006 | Schuermann ........ A61B 17/221 606/2.5 |
| 2006/0269512 A1 | 11/2006 | McDougal et al. |
| 2007/0231393 A1 | 10/2007 | Ritter et al. |
| 2008/0065012 A1 | 3/2008 | Hebert et al. |
| 2008/0103481 A1 | 5/2008 | Vogel et al. |
| 2009/0136594 A1 | 5/2009 | McLeroy et al. |
| 2009/0162411 A1 | 6/2009 | Buensuceso et al. |
| 2010/0121188 A1 | 5/2010 | Sandhu et al. |
| 2011/0097367 A1 | 4/2011 | Wallrapp et al. |
| 2012/0108676 A1 | 5/2012 | Smyth et al. |
| 2016/0074561 A1 | 3/2016 | Grunwald et al. |

FOREIGN PATENT DOCUMENTS

| | | |
|---|---|---|
| CA | 2 710 986 A1 | 7/2009 |
| CN | 101700422 A | 5/2010 |

(Continued)

OTHER PUBLICATIONS

Geppert et al., "Uptake of dimercaptosuccinate-coated magnetic iron oxide nanoparticles by cultured brain astrocytes," *Nanotechnology*, 22(14): 10 pages, Feb. 24, 2011.

(Continued)

*Primary Examiner* — Shaojia A Jiang
*Assistant Examiner* — Dale R Miller
(74) *Attorney, Agent, or Firm* — Seed IP Law Group LLP

(57) ABSTRACT

Primarily described are gel-forming systems, consisting of or comprising a composition (A), comprising one or several cationically crosslinkable polymer(s), and a composition (B), comprising one or several crosslinking agent(s) for crosslinking the cationically crosslinkable polymer(s) for use in a method for removing urinary calculi and/or fragments thereof, more particularly kidney stones and/or fragments thereof, from a region of the urinary tract, more particularly a kidney, that contains urinary calculi and/or fragments thereof, more particularly kidney stones and/or fragments thereof, that are to be removed, with the following steps: (i) providing the compositions (A) and (B), (ii) introducing the compositions (A) and (B) into a region of the urinary tract, more particularly the kidney, that contains urinary calculi and/or fragments thereof, more particularly kidney stones and/or fragments thereof, that are to be removed, under conditions enabling crosslinking of the cationically crosslinkable polymer(s) upon contact of composition (A) with composition (B) so that a crosslinked gel is formed that partly or fully surrounds the urinary calculi and/or fragments thereof, more particularly kidney stones and/or fragments thereof, that are to be removed, (iii) removing the crosslinked gel together with the urinary calculi and/or fragments thereof, more particularly kidney stones and/or fragments thereof, that are surrounded by it from the urinary tract, more particularly the kidney.

9 Claims, 2 Drawing Sheets

(56) References Cited

FOREIGN PATENT DOCUMENTS

| | | |
|---|---|---|
| JP | 2004-524898 A | 8/2004 |
| JP | 2010-510814 A | 4/2010 |
| WO | 98/12228 A1 | 3/1998 |
| WO | 01/05443 A1 | 1/2001 |
| WO | 02/18448 A2 | 3/2002 |
| WO | 02067788 A1 | 9/2002 |
| WO | 2004/080343 A2 | 9/2004 |
| WO | 2005/037062 A2 | 4/2005 |
| WO | 2006119009 A1 | 11/2006 |
| WO | 2008042756 A2 | 4/2008 |
| WO | 2008/103891 A2 | 8/2008 |
| WO | 2009/070766 A2 | 6/2009 |

OTHER PUBLICATIONS

Cha et al., "Bulk adhesive strength of recombinant hybrid mussel adhesive protein," *Biofouling* 25(2):99-107, Feb. 2009.

Le Renard et al., "The in vivo performance of magnetic particle-loaded injectable, in situ gelling, carriers for the delivery of local hyperthermia," *Biomaterials* 31:691-705, 2010.

Leung et al., "Characteristics and Properties of Carboxylated Cellulose Nanocrystals Prepared from a Novel One-Step Procedure," *small* 7(3):302-305, 2011.

Tan et al., "In Vitro Comparison of Prototype Magnetic Tool with Conventional Nitinol Basket for Ureteroscopic Retrieval of Stone Fragments Rendered Paramagnetic with Iron Oxide Microparticles," *The Journal of Urology* 188:648-652, Aug. 2012.

\* cited by examiner

GEL-FORMING SYSTEM FOR REMOVING URINARY CALCULI AND FRAGMENTS THEREOF

BACKGROUND

Technical Field

The present invention primarily relates to a gel-forming system, more particularly an adhesive-forming system, for use in a method for removing urinary calculi and/or fragments thereof, more particularly kidney stones and/or fragments thereof, from the body, more particularly from the urinary tract. More particularly, the present invention relates to a gel-forming system, more particularly to an adhesive-forming system, consisting of or comprising a composition (A), comprising one or several cationically crosslinkable polymer(s), and a composition (B), comprising one or several crosslinking agent(s) for crosslinking the cationically crosslinkable polymer(s), so that upon contact of composition (A) with composition (B) in a region of the urinary tract, more particularly in the kidney, that contains urinary calculi and/or fragments thereof, more particularly kidney stones and/or fragments thereof, a crosslinked gel is formed that partly or fully surrounds the urinary calculi and/or fragments thereof, more particularly the kidney stones and/or fragments thereof.

Furthermore, the present invention relates to a gel-forming system, more particularly an adhesive-forming system, consisting of or comprising compositions (A) and (B) as described herein, as well as in addition comprising magnetizable particles for partly or fully surrounding urinary calculi and/or fragments thereof, more particularly kidney stones and/or fragments thereof, by forming a crosslinked gel upon contact of composition (A) with composition (B), wherein the crosslinked gel contains the magnetizable particles.

The present invention thus also relates to a crosslinked gel, more particularly an adhesive, for partly or fully surrounding urinary calculi and/or fragments thereof, more particularly kidney stones and/or fragments thereof, wherein the crosslinked gel contains magnetizable particles and is producible or produced by means of providing a composition (A) and (B) as described herein, as well as optionally a composition (C), wherein composition (A) and/or composition (B) and/or composition (C) comprise magnetizable particles, and contacting compositions (A) and (B) (as well as (C), if applicable) under conditions that enable crosslinking of the cationically crosslinkable polymer(s) so that a crosslinked gel is formed.

Description of the Related Art

Urinary calculi can be formed in the revulsive urinary tract. A urinary obstruction first leads to strong, labor-like pain (so called renal colic). If left untreated, urinary calculi can lead to serious health problems (loss of renal function, inflammation) and vitally endanger the patient (sepsis during infected urinary calculus-caused urinary transport disorder). From an epidemiological point of view, urinary calculus conditions are one of the most prevalent diseases afflicting mankind, whose incidence in Germany amounted to 1.45% in the year 2000, which in turn corresponds to 1,200,000 new cases per year. In Germany alone a total of ca. 750,000 cases of treatment can be expected per year. The number of treatments for removing calculi in Germany is estimated to be about 400,000 per year, about half thereof being treatments of recurring calculi. The numbers referred to can be extrapolated to a millionfold implementation of such treatments worldwide. With a sum of over 1.5 billion Euros, urinary calculus conditions represent a substantial cost factor for the German healthcare sector.

If the calculi do not exit the body by natural routes or if medicinal indications for immediate therapy exist, endoscopy (minimally invasive endoscopy techniques) represents the therapeutic "gold standard" besides the extracorporeal shock wave treatment (ESWT). In light of increasing evidence for worse results of ESWT, endoscopic methods are preferably used. It can be assumed that currently 60-70% of calculi patients are treated endoscopically. This tendency is increasing. With the help of endoscopic techniques, calculi are locally crushed and removed. To date, small residual fragments (<2 mm), that cannot be removed effectively during treatment, pose an unsolved problem. Remaining fragments of kidney stones act as "crystal seeds" from which new calculi are formed with a likelihood of 70%. This in turn leads again to medicinal problems and need for treatment.

About 30 million people in Europe are suffering from kidney stones (ca. 5% of the population), and the frequency of occurrence of urinary calculi conditions shows an increasing tendency in industrialized countries. The risk to be repeatedly affected by kidney stones after recovery is particularly high (ca. 60%). Medicinal complications that can arise in connection with kidney stones are loss of renal function and infectious complications all the way to sepsis. This results in a severe burden for the healthcare systems.

One option to specifically navigate the position and distribution of substances or objects in the body is the utilization of magnetic interactions. For this purpose, the target substances and target objects, respectively, have to be magnetized accordingly. Magnetic (nano)particles have already proven to be suitable in different biomedical applications, since they have high biocompatibility and can be modified with different functional groups. Thus, magnetic particles are used, for example, to transport active substances to a desired site of action in the body. Hence, therapeutic and diagnostic substances can be used efficiently and damages in healthy tissues caused by potential side effects can be minimized.

In this context, US 2007/0231393 describes a method in which magnetic drug carrier particles are positioned in the body by means of an external magnetic field.

US 2009/0136594 is concerned with a method to magnetize biological particles by contacting them with magnetic particles which are modified such that they are able to bind specifically to the biological particles. Kidney stones and fragments thereof can be magnetized as one possible application to remove them from the body by means of equipment that magnetically attracts such particles. In order to specifically bind calcium-based biominerals (such as, for example, kidney stones), the particles are modified with certain calcium-binding proteins or fragments thereof.

Larger calculi usually cannot be removed by means of a minimally invasive procedure and therefore have to be smashed into smaller fragments first and have to be dissolved completely or at least partly, respectively. A method for treatment of kidney stones through specific dissolution of the deposits by using quaternary ammonium salts is described, for example, in U.S. Pat. No. 5,244,913.

Another possibility for treating kidney stones without smashing them beforehand is specified in US 2006/0269512. Here, the natural peristalsis is used to press a polymer clot through a lumen and to thereby remove the calculus from the lumen. The polymer clot can be formed in situ through temperature or pH change or through ionic interactions.

Lithotripsy is a method where kidney stones are smashed by means of extracorporeal shock waves or endoscopically inserted laser or compressed air probes. Thereby, fragments of different sizes are formed which can be removed with the aid of grasping instruments or can be flushed out. One problem occurring during lithotripsy is that the fragments are able to spread or reach regions that are hard to access.

WO 2005/037062 relates to a method in which kidney stones are enclosed (not enclosed in) in a certain area with the aid of a polymer clot, whereby damages to the tissues through the formed fragments during smashing can be prevented to a large extent. According to WO 2005/037062, a gel-forming liquid, for example a thermosensitive polymer, is injected into the lumen on at least one side of the kidney stone, which forms a gel clot at body temperature. The polymer thereby usually does not get into contact with the kidney stone, but serves to increase the efficiency of the lithotripsy by preventing shifting of the kidney stone and by protecting the surrounding tissue from damage through fragmentation.

According to US 2008/0103481, a biocompatible polymer clot is used more particularly to prevent a backwards shift of kidney stones or fragments thereof during lithotripsy and thereby to minimize the damage to the surrounding tissues.

An approach to remove objects, such as for example blood clots, from the body using an adhesive is specified in US 2008/0065012. In the process, the adhesive is distributed on a surface and inserted into the body with the aid of a catheter. When is object is adhered to the surface, the catheter is removed and takes the object with it.

Adhesives based on biological macromolecules and more particularly gel-forming polymer systems are used increasingly in medical technology. Thereby, their high biocompatibility is one of their most important selection criteria.

Thermosensitive or ionically polymerizable polymers are used, for example, to stop the blood flow from injured blood vessels. WO 2008/103891 specifies a method in which the outflow of biological fluids from tissues or vessels can be controlled through in situ formation of a polymer clot.

WO 01/05443 relates to an adhesive protein foam and its use for surgical and therapeutic applications. The foam consists of a liquid protein matrix and a biocompatible gas and serves for covering and protecting, respectively, injured tissue or for connecting implanted tissue with biological tissue.

WO 02/18448 describes the pharmaceutical use of percarboxylated polysaccharides in the manufacture of biomaterials for surgical and biomedical applications. Such material are especially well suited for use in the body since they are recognized as being endogenous and do not trigger any immune rejection reaction. Therefore, they can be used as coatings for implants.

A method for encapsulation of renal tissue in spheres of biocompatible polymers is described in US 2009/0162411. The aim of such encapsulation is to maintain renal tissue implants, which can be injected into a patient who suffers from a renal function disorder in order to support renal function.

Calcium alginate as a biocompatible hydrogel polymer for closing skull openings after open brain surgery is disclosed in WO 2004/080343.

The suitability of polysaccharide-containing polymers for binding biologically active molecules or whole cells in the field of organ transplantation and of artificial tissue replacement is described in WO 1998/012228.

Alginates are also used as fillers for supporting skin and muscles in the medicinal and cosmetic field. In US 2011/0097367 applications are described in which monolithic alginate implants are formed in situ by means of injection of a pure, high molecular weight alginate solution into the tissue and spontaneous crosslinking Crosslinking takes place through $Ca^{2+}$ ionic bridges without the need of having to add additional crosslinking agents. The described alginate implants are suitable for the treatment of wrinkles or different conditions in which the muscular structure is weakened.

In U.S. Pat. No. 6,663,594 B2, a method for immobilization of an object in the body, for example a kidney stone, is described, wherein a gel-forming liquid is injected into the body. Upon contact with the object, a gel is formed, which at least partly captures and immobilizes the object. The immobilization serves for being able to subsequently fragment the object without risking distribution of the fragments and for removing the object or fragments, respectively, from the body with an endoscopic tool. The gel thereby prevents the object or fragment, respectively, from shifting and not being able to be grasped with the tool. After removal of the object or fragments, respectively, the gel is dissolved or extracted with the aid of an endoscopic tool. A disadvantage of the method is that during smashing of the kidney stones the gel that is already set might be destroyed and thereby fragments can be released again or that discrete fragments might escape from the polymer. In addition, the described procedure is very time-consuming, since the calculi or fragments thereof have to be grasped and removed individually. Consequently, individual calculus fragments will remain behind with a relatively high likelihood.

More particularly, one problem of lithotripsy is the occurrence of medium sized calculus fragments (more particularly <2 mm), also called "gravel", since these fragments can neither be grasped efficiently nor flushed. Residual fragments of this size slide through the mesh of the grasping instruments (grasping forceps or baskets) and render the extraction of gravel very time-consuming and with larger amounts of calculi practically unfeasible. To date, no technology has been successfully established to fully remove the medium size and small calculus fragments. Such kidney stone fragments remaining behind, however, in a large percentage of cases lead to the formation of new kidney stones, since the fragments serve as "crystal seeds".

In order to ensure complete removal of fragments of any size, a new method has to be developed which is suited to ideally reliably capture all of the fragments. Thereby, the problems and difficulties (partly mentioned above) that are entailed in the methods known in the state of the art, shall preferably be avoided.

BRIEF SUMMARY

The primary object of the present invention was to provide a system that is used for being able to reliably extract urinary calculus fragments, in particular, from the body.

More particularly, it was an object of the present invention to provide a gel-forming system that is used for being able to extract small and medium sized urinary calculus fragments from the body.

It was a further object of the present invention to specify a method for removing the urinary calculus fragments, more particularly kidney stone fragments, from the body with minimally invasive procedures.

Further objects of the present invention arise from the following description as well as, more particularly, from the attached patent claims.

The primary object is solved according to one aspect of the present invention by a gel-forming system, more particularly an adhesive-forming system, consisting of or comprising a composition (A), comprising one or several cationically crosslinkable polymer(s), and a composition (B), comprising one or several crosslinking agent(s) for crosslinking the cationically crosslinkable polymer(s) for use in a method for removing urinary calculi and/or fragments thereof, more particularly kidney stones and/or fragments thereof, from a region of the urinary tract, more particularly the kidney, that contains urinary calculi and/or fragments thereof, more particularly kidney stones and/or fragments thereof, that are to be removed, with the following steps:

(i) providing the compositions (A) and (B), (ii) introducing the compositions (A) and (B) into a region of the urinary tract, more particularly the kidney, that contains urinary calculi and/or fragments thereof, more particularly kidney stones and/or fragments thereof, that are to be removed, wherein composition (B) is preferably introduced before composition (A), under conditions enabling crosslinking of the cationically crosslinkable polymer(s) upon contact of composition (A) with composition (B), so that a crosslinked gel is formed that partly or fully surrounds the urinary calculi and/or fragments thereof, more particularly kidney stones and/or fragments thereof, that are to be removed, (iii) removing the crosslinked gel together with the urinary calculi and/or fragments thereof, more particularly kidney stones and/or fragments thereof, that are surrounded by it from the urinary tract, more particularly the kidney.

Within the scope of the present invention, a region of the urinary tract or the kidney, respectively, is to be understood as meaning the pelvicocaliceal system, in particular, as well as the revulsive urinary paths, ureter, bladder or urethra.

"Urinary calculus fragments" are in connection with the present invention to be understood as meaning fragments of urinary calculi, more particularly kidney stones, that formed, in particular, by means of smashing urinary calculi (lithotripsy).

By means of embedding of the urinary calculi according to the invention and subsequent extraction of the "adhesive composite", preferably fragments of any size can be fully removed and thereby repeated calculus formation can be prevented.

The polymers or polymer units, respectively, of composition (A) are preferably crosslinked via ionic interactions (see composition (B)). Therefore, a multitude of macromolecules that occur as ligands of monovalent or multivalent cations and are able to form chelate complexes are suitable for application according to the invention. These include more particularly hydrogels, biocompatible sugar-based (e.g., modified celluloses) or proteinogenic adhesives or fibrin-based or collagen-based systems (particularly preferred polymers are described below).

Polyphenolic proteins, for example, are able to set via crosslinks of their protein scaffold with the aid of a catechol oxidase. Such crosslinks can also be achieved in vitro, for example, with the aid of metal ions. The use of hybrid systems is also conceivable that are based on a combination of synthetic polymers with phenolic amino acids. The post-translational amino acid 3,4-dihydroxyphenylalanine (DOPA), for example, is specifically suited for polymer modification, because of its diverse possibilities for reaction with different functional groups, and corresponding gel systems are characterized by improved adhesive and cohesive properties.

Suitable cations preferably serve as crosslinking agents of composition (B). Advantageously, this usually concerns cations that naturally occur in physiological systems. Advantageously, no additional (aggressive) reagents have to be added to start the crosslinking reaction under physiological conditions. In addition, advantageously no undesired byproducts are formed.

Preferred according to the invention are such systems that are able to set under physiological conditions. In order to form stable crosslinks via cationic bridges, it is advantageous if the polymers of composition (A) have functional groups (in sufficient number) that are available as negatively charged units even at (slightly) acidic pH. In some systems, the degree of crosslinking or the speed of crosslinking, for example, can be controlled via influenceable factors such as concentration or pH-value.

According to a preferred embodiment composition (A) and/or composition (B) contain chitosan. Particularly preferably composition (B) contains chitosan.

Compositions (A) and (B) can be introduced one after the other or together, whereby it is preferred that composition (B) is introduced before composition (A) to guarantee a suitable distribution and complete embedding of all of the urinary calculus fragments, more particularly kidney stone fragments, before start of and during crosslinking, respectively.

The solidified gel preferably has a sufficient stability and flexibility to be subsequently removed from the body with the smallest possible effort, preferably in one piece. The gel-calculus fragment-conglomerate(s) preferably has or have a diameter of 4 mm or less, respectively.

A system according to the invention can additionally contain further components. Substances, for example, that support the gel formation and/or embedding of the urinary calculus fragments, more particularly kidney stone fragments, can be added to compositions (A) and/or (B) and/or to one or several further compositions of a system according to the invention. Such substances may be, e.g., crosslinkers for increasing the stability of the gel.

According to a preferred embodiment, composition(s) (A) and/or (B) and/or one or several further composition(s) of a system according to the invention additionally contain(s) one or several dye(s) that facilitate to visualize the set gel and one, both, several or all of the used compositions (before setting) endoscopically.

According to a preferred embodiment of the present invention, the or one, several or all of the cationically crosslinkable polymer(s), respectively, of composition (A) is or are selected from the group consisting of polysaccharides, more particularly polysaccharides with deprotonated or deprotonatable functional groups, preferably carboxy groups, preferably polysaccharides from the group of polyuronides, particularly preferred polysaccharides from the group of alginates and pectins.

Polysaccharides such as alginates and pectins are particularly suited for use in the body, since they do not trigger any inflammatory reactions or immune rejection and involve a minimal risk of tissue trauma. Additionally, they are biodegradable and have a large amount of carboxylic acid groups that are able to form chelate complexes with multivalent cations. Advantageously, they are able to crosslink under water and at physiological temperatures and can be handled easily in solution. The crosslinking thereby takes place quickly but without agglutinating delicate renal tubules or the endoscopy instruments. The formed gels exhibit sufficient stability and flexibility to be extracted together with the urinary calculus fragments.

According to a further preferred embodiment of the present invention, the or one, several or all of the crosslinking agent(s), respectively, of composition (B) is or are selected from the group consisting of divalent and trivalent cations, preferably iron and calcium ions.

Iron and calcium ions are cations that occur naturally in physiological systems and that can be easily administered in the form of biologically compatible solutions. They have a suitable coordination chemistry and are able to form stable chelate complexes for crosslinking According to a further preferred embodiment of the present invention, composition (B) has an acidic pH-value, preferably a pH in the range of 3.5 to 4.5.

At a pH in the range of 3.5 to 4.5 the cations exist freely in solution and are therefore available for complexation. Advantageously, in this pH range the acid groups that are located at the polysaccharide are deprotonated to a large extent, whereby an effective crosslinking reaction takes place. If a buffered solution (at a pH of approx. 4) is provided in the region of the urinary calculus fragments, more particularly kidney stone fragments, that are to be removed, the introduction of the polysaccharide-containing composition (A) leads to a reduction of the solubility (coacervation). The process of coacervation takes a certain amount of time while the urinary calculus fragments are embedded. Advantageously, the speed of the crosslinking reaction is thereby also controllable via the pH of the used compositions.

According to a further preferred embodiment of the present invention relates to a gel-forming system, more particularly an adhesive-forming system as described above, wherein the gel-forming system additionally contains magnetizable particles, wherein the magnetizable particles are part of composition (A) and/or composition (B)
and/or
the polymerizable system in addition comprises a composition (C) that contains magnetizable particles, wherein then in step (i) composition (C) is also provided besides compositions (A) and (B) and in step (ii) composition (C) is introduced as well, time-delayedly or at the same time, with composition (A) or composition (B), so that the crosslinked gel additionally contains magnetizable particles.

The addition of magnetizable particles opens up a new and advantageous method to remove the set "adhesive composite" (gel-calculus fragment-conglomerate) from the body by utilizing the magnetic properties. A magnet fishing instrument or more particularly a magnetic retrieval basket can be used for instance, which combines the advantages of an anchor and of a usual retrieval basket.

According to a preferred embodiment of the present invention, the magnetizable particles are selected from particles comprising or consisting of ferromagnetic elements such as iron, nickel and cobalt as well as alloys such as AlNiCo, SmCo, $Nd_2Fe_{14}B$, $Ni_{80}Fe_{20}$, NiFeCo and/or oxides thereof such as iron oxide particles, more particularly iron oxide nanoparticles made of $Fe_3O_4$ and/or $\gamma\text{-}Fe_2O_3$.

Iron oxide particles haven proven to be suitable for medical technology and pharmaceutical applications, e.g., as intravenously administered contrast agents for magnetic resonance imaging or for tumor therapy. To increase the biocompatibility and colloidal stability, such particles are usually coated with, e.g., dextranes, polyvinyl alcohols, dimercapto succinic acid and others.

Moreover, the iron oxide particles provide a dark color to the adhesive, which enables a simpler handling according to visual aspects in contrast to the unmodified gel which is almost colorless (cf., concerning this the remarks above in connection with optionally contained dyes).

According to a preferred embodiment of the present invention, the method for removing urinary calculus fragments, more particularly kidney stone fragments, comprises the following additional step, which takes place chronologically before step (ii):

Fragmentation of one or several urinary calculus/calculi, more particularly kidney stones, in the urinary tract, more particularly in the kidney, so that two or several, preferably a plurality of urinary calculus fragments, more particularly kidney stone fragments, is or are formed.

The gravel that is formed during smashing of urinary calculi can be removed particularly efficiently by using the gel-forming system according to the invention. In contrast to the techniques described in the state of the art, medium sized fragments are also reliably captured during gel-formation and can ideally be completely removed from the body.

A further aspect of the present invention relates to a gel-forming system, more particularly an adhesive-forming system, consisting of or comprising a composition (A), comprising one or several cationically crosslinkable polymer(s), and a composition (B), comprising one or several crosslinking agent(s) for crosslinking the cationically crosslinkable polymer(s), as well as in addition magnetizable particles, wherein the magnetizable particles are part of composition (A) and/or part of composition (B) and/or wherein the polymerizable system comprises in addition a composition (C) that contains magnetizable particles, for partly or fully surrounding urinary calculi and/or fragments thereof, more particularly kidney stones and/or fragments thereof, in the urinary tract, more particularly in the kidney, by means of forming a crosslinked gel upon contact of composition (A) with composition (B) (as well as additionally composition (C), if applicable), wherein the crosslinked gel contains magnetizable particles.

The magnetizable particles can therefore get into the gel-forming system by any means. They can both be part of one or both of the compositions (A) and/or (B) as well as be added as part of an additional composition (C).

According to a preferred embodiment of this aspect of the present invention, composition (A) and/or composition (B) (additionally) contain(s) chitosan. Particularly preferably composition (B) contains chitosan.

According to a (further) preferred embodiment of the present invention, the or one, several or all of the cationically crosslinkable polymer(s), respectively, of composition (A) is or are selected from the group consisting of polysaccharides, more particularly polysaccharides with deprotonated or deprotonatable functional groups, preferably carboxy groups, preferably polysaccharides from the group of polyuronides, particularly preferred polysaccharides from the group of alginates and pectins.

In this connection, what has been already said above regarding the polysaccharides of composition (A) applies accordingly.

According to a further preferred embodiment of the present invention, the or one, several or all of the crosslinking agent(s), respectively, of compound (B) is or are selected from the group consisting of divalent and trivalent cations, preferably iron and calcium ions.

Also regarding the crosslinking agents of composition (B), what has been said above applies accordingly.

According to a further preferred embodiment of the present invention, composition (B) has an acidic pH-value, preferably a pH in the range from 3.5 to 4.5.

What has been said above regarding the pH-value of a composition (B) described herein applies here accordingly as well.

According to a further preferred embodiment of the present invention, the magnetizable particles are selected from particles comprising or consisting of ferromagnetic elements such as iron, nickel and cobalt as well as alloys such as AlNiCo, SmCo, $Nd_2Fe_{14}B$, $Ni_{80}Fe_{20}$, NiFeCo and/or oxides thereof such as iron oxide particles, more particularly iron oxide nanoparticles made of $Fe_3O_4$ and/or $\gamma\text{-}Fe_2O_3$.

Again, what has been said above regarding the magnetizable particles applies accordingly.

A further aspect of the present invention relates to a crosslinked gel, more particularly to an adhesive, for partly or fully surrounding urinary calculi and/or fragments thereof, more particularly kidney stones and/or fragments thereof, in the urinary tract, more particularly in the kidney, wherein the crosslinked gel contains magnetizable particles and is producible or produced by means of (i) providing a composition (A), comprising one or several cationically crosslinkable polymer(s), and a composition (B), comprising one or several crosslinking agent(s) for crosslinking of the cationically crosslinkable polymer(s) as well as, optionally, a composition (C), wherein composition (A) and/or composition (B) and/or, if present, composition (C) contain magnetizable particles, (ii) contacting compositions (A) and (B) (as well as (C), if applicable) under conditions that enable crosslinking of the cationically crosslinkable polymer(s), so that a gel is formed.

The manufacture of a crosslinked gel according to the invention occurs by contacting compositions (A) and (B) (as well as (C), if applicable). The setting preferably takes place in a region of the urinary tract, more particularly the kidney, in which urinary calculi and/or fragments thereof, more particularly kidney stones and/or fragments thereof, more particularly of small and medium size (preferably with an average mean diameter of 0.1 to 4 mm, preferably of 0.2 to 3 mm, particularly preferably of 0.5 to 2 mm) are present, so that these can be fully or at least partly surrounded on site. The crosslinked gel according to the invention preferably sets under physiological conditions and has sufficient stability and flexibility to preferably be extracted from the body in one piece. Further preferred embodiments arise from the remarks above.

According to a preferred embodiment of the crosslinked gel, more particularly of the adhesive, compound (A) and/or compound (B) contain chitosan. Particularly preferably compound (B) contains chitosan.

A particularly preferred embodiment of the present invention relates to a crosslinked gel, more particularly an adhesive, as described above, wherein the or one, several or all of the cationically crosslinkable polymer(s), respectively, of composition (A) is or are selected from the group consisting of polysaccharides, more particularly polysaccharides with deprotonated or deprotonatable functional groups, preferably carboxy groups, preferably polysaccharides from the group of polyuronides, particularly preferred polysaccharides from the group of alginates and pectins.

In this connection, what has been said above regarding the polysaccharides of composition (A) applies accordingly.

A further preferred embodiment of the present invention relates to a crosslinked gel, more particularly an adhesive, as described above, wherein the or one, several or all of the crosslinking agent(s), respectively, of composition (B) is or are selected from the group consisting of divalent and trialent cations, preferably iron and calcium ions.

Also regarding the crosslinking agents of composition (B), what has been said above applies accordingly.

Within the scope of the present invention a method for removing urinary calculi and/or fragments thereof, more particularly kidney stones and/or fragments thereof, from a region of the urinary tract, more particularly the kidney, that contains urinary calculi and/or fragments thereof, more particularly kidney stones and/or fragments thereof, is described herein as well, consisting of or comprising the following steps:

(i) Providing a composition (A), comprising a cationically crosslinkable polymer, preferably a polysaccharide with deprotonated carboxy groups, particularly preferably a polysaccharide selected from the group of polyuronides, more particularly an alginate or pectin, and a composition (B), comprising a crosslinking agent for crosslinking the cationically crosslinkable polymer(s), more particularly iron and/or calcium ions, wherein composition (A) and/or (B) preferably contain in addition magnetizable particles, for example iron oxide particles, or wherein a composition (C) is additionally provided that contains magnetizable particles, for example iron oxide particles, (ii) introducing compositions (A) and (B) as well as (C), if applicable, into the region of the urinary tract, more particularly the kidney, that contains urinary calculi and/or fragments thereof, more particularly kidney stones and/or fragments thereof, that are to be removed, at the same time or time-delayedly, wherein composition (B) is preferably introduced before composition (A), under conditions enabling crosslinking of the cationically crosslinkable polymer(s) upon contact of composition (A) with composition (B) (as well as composition (C), if applicable), so that a crosslinked gel is formed that surrounds the urinary calculus fragments, more particularly kidney stone fragments, partly or fully and in addition contains magnetizable particles, (iii) removing the crosslinked gel together with the urinary calculi and/or fragments thereof, more particularly kidney stones and/or fragments thereof, that are surrounded by it, from the urinary tract, more particularly the kidney.

In the following, the present invention is explained in more detail on the basis of some selected examples.

DETAILED DESCRIPTION

EXAMPLE 1

Figure 1:
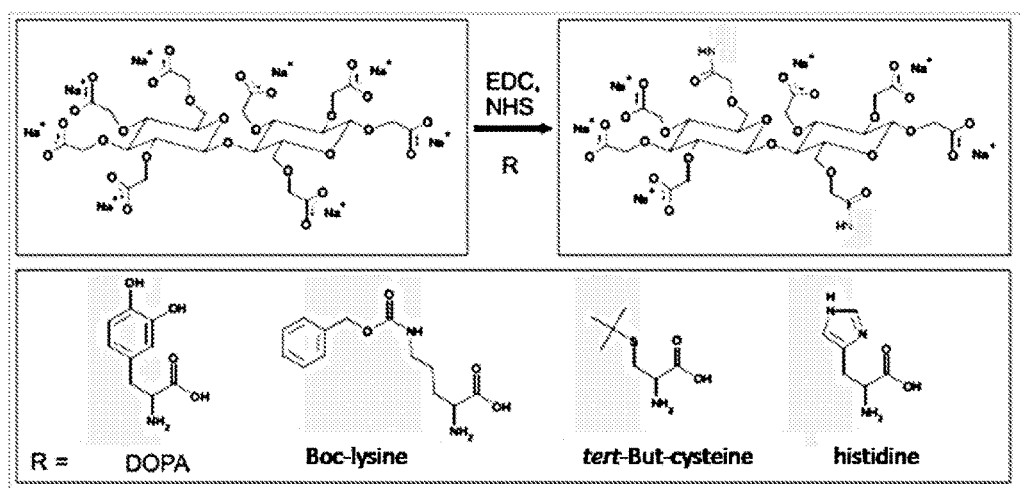
FIG. 1: Modification strategy for CMC (carboxymethyl cellulose) with DOPA and one of the amino acids summarized under R (bottom box); the used amino acids are partially protected; from left to right: 3,4-Dihydroxyphenylalanine, N-Boc-lysine, t-butyl-cysteine, histidine.

Manufacture of Compositions (A), (B) and (C)

For manufacture of an exemplary composition (A), 2 g of alginate are dissolved in 200 mL of water.

For manufacture of an exemplary composition (B), an aqueous solution of $FeCl_3$ (1M) as well as a water-based chitosan solution (0.32 wt.-%, pH 6) and a solution of oxalic acid in water (1M) are initially produced. Approx. 5 drops of the oxalic acid solution are added to 3 mL of the chitosan solution and to this mixture 0.5 mL of iron chloride solution are added.

For manufacture of an exemplary composition (C), a particle suspension in water or physiological buffer containing 4 to 40 mM iron (0.35 to 3.5 per liter) is prepared (M. Geppert et al., Nanotechnology 22 (2011) 145101). This solution is added to A or B to 1% to 50%.

EXAMPLE 2 (EXPERIMENT)

Gel Formation with Modified Biopolymers Using an Amino Acid-Carboxymethyl Cellulose-Hybrid as an Example The alginate-like sugar derivative sodium carboxymethyl cellulose (CMC) was functionalized with the amino acids DOPA, lysine, cysteine and histidine (FIG. 1), respectively. The DOPA-modified CMC was mixed with the amine functional polysaccharide chitosan and the hydrogel that is formed via electrostatic interaction between the differently charged sugars is examined for its adhesive properties. Moreover, all of the amino acid-cellulose-hybrids were mixed to obtain jellies and the composite strength upon adhesion to titanium was tested. The aim of the experiments was to improve the adhesive properties of the (exemplary) hybrids in a moist environment in order to alter the inclusion of the urinary calculi and fragments thereof, respectively, and the flexibility of the adhesive.

Two different substitution grades were aimed at for the functionalization with DOPA. Each mole of CMC has got eight moles of acetate groups. Related to it, it was modified with half per mil (PA-S6) on the one hand and with 0.3 equivalents of DOPA (PA-S7) on the other hand.

The sodium carboxymethyl cellulose (CMC) was firstly functionalized with the amino acid 3,4-dihydroxyphenylalanine (DOPA) according to an unconventional procedure [1]. Therefore, first of all 2 g of CMC (2 mmol) were dissolved in 30 mL of dd-water over the course of 90 min at 40° C. The pH of the solution of approx. 7 was adjusted to a pH of 4-5 with an aqueous HCl-solution (2 N). 19 mg of EDC (0.1 mmol) and 12 mg of NHS (0.1 mmol) were added to the viscous solution. After 30 min, 20 mg (0.1 mmol) of DOPA, dissolved in 1.5 mL of dd-water, were added dropwise and slowly over a fine syringe while the solution was stirring continuously. The solution was kept stirring overnight.

10 mL of this solution were removed (PA-S6). A further 2 mL of the solution were lyophilized for ATR analysis. The remainder of the solution (ca. 18 mL) was reactivated for 30 min with 1.1 g of EDC (5.8 mmol) and 0.7 g of NHS (6.1 mmol). An acidic solution of 0.6 g of DOPA (3 mmol) in 10 mL of dd-water and 1 mL of an aqueous HCL solution (2 N) were added slowly via a fine syringe, as done previously for PA-S6, while ensuring good mixing. An ATR was obtained of this solution PA-S7 as well.

The product (PA-S6) was mixed in equal parts with a fresh 0.3% chitosan solution (pH 6). The mixture was divided into two vessels. To one of the two mixtures, 0.5 v % of a fresh laccase solution (1 mg/mL) was added. Both mixtures were mixed well and subsequently locked lying on top of a heatable agitating plate. The shaker was programmed to a run time of four hours at 47° C. and 650 rpm.

The DOPA-CMC-chitosan solution (PAChi) and the DOPA-CMC-chitosan solution in presence of the peroxidase laccase (PAChiLA) that initiates the crosslinking of the catechols, were incubated in order to alter the properties of the expected hydrogels. Thereby, elastic hydrogels formed in both reaction vessels.

Figure 2:
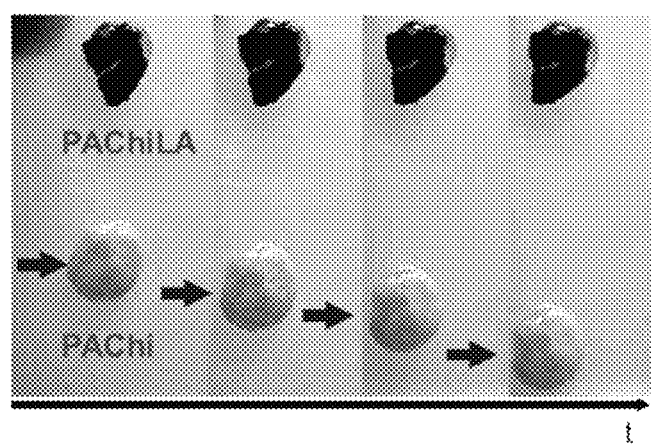
FIG. 2: Photo documentation of a mixture of catechol-modified carboxymethyl cellulose (blackish-brown hydrogel, top) and of the enzyme-free reference hydrogel (ivory, bottom, represented in grey here) on parafilm under the influence of gravity over time.

Both samples with (PAChiLA) and without laccase (PAChi) were examined regarding their different adhesion potentials. Therefore, one sample (PAChiLA; PAChi) was applied to parafilm, respectively, and the test installation was aligned orthogonally. Thereby, gravity acts on the adhesive surface between the cellulose hydrogel and the surface of the parafilm. The paths lengths that the samples covered due to the gravity that acted on them over time were recorded photographically (FIG. 2).

The hydrogel of the reference was characterized by an ivory-like color, whereas the catechol containing hydrogel that was polymerized with the aid of laccase had a brownish-black color. This discoloration is characteristic for polyphenols and is indicative of an oxidation of the DOPA group on the CMC polymer backbone.

Through the amines offered by the chitosans, the formation of a covalent network as a result of Michael reactions with amines and radical additions might have taken place. The formation of a hydrogel for the reference of the catechol containing cellulose with chitosan without enzyme can be explained by an electrostatic interaction between the carboxylic acids of the carboxy cellulose that are still available and the amines of the chitosan. Subsequently, both hydrogels were examined in a functional experiment regarding the differences in their macroscopic adhesive properties on parafilm. Under the influence of the force vector gravity, the interaction forces gave way to a varying degree as can be read from the covered path lengths. The results of the photo documentation show a stronger adhesion of the crosslinked hydrogel to parafilm in comparison with the reference that is not covalently crosslinked and was incubated without enzyme.

These results support the assumption that the DOPA-CMC-chitosan (PAChi), which is present in an oxidized from, may not be a covalently crosslinked hydrogel. The connection between adhesion and the changes in the sugar matrix provoked by the catechol open up controllable properties of the hydrogel. The purely electrostatically interacting networks rearrange themselves within the hydrogel and give way under the influence of the force vector. This phenomenon is known as creep behavior for thermoplastics.

The enzymatically oxidized DOPA-CMC-chitosan (PAChiLA) has got covalent crosslinks within the hydrogel and as a result of acting shear forces is limited in reorientation. Furthermore, interactions between the polyphenols in the hydrogel network with the polyolefins and paraffin waxes inside the parafilm might occur.

The functionalization of the carboxymethyl cellulose was extended beyond the catechol DOPA to three further amino acids (FIG. 1). The aim of this diversification was to improve the adhesive properties in moist environment through combination of these hybrids For the synthesis, first of all 13.5 g of CMC (14 mmol) were weighed into a 1 L beaker and dissolved in 550 mL of dd-water under slight stirring at 40° C. After 90 min the clear yellowish solution was cooled to room temperature under stirring. As described above, the present CMC was partly converted into the N-succinimide active ester by using EDC/NHS. After approx. 40 min, the reaction mixture was divided in five Erlenmeyer flasks á 83 mL (ca. 2 g CMC). Then, 40 mmol of the amino acid were added to one of the reaction vessels, respectively.

76 mg of DOPA or 60 mg of histidine, respectively, were solvated beforehand in 100 µL HCl (2N) and 1900 µL dd-water, respectively. 95 mg of H-Lys(Boc) or 83 mg of H-Cys(tBut)-OH*HCl, respectively, had to be taken up in 2 mL of dd-water in order to preserve the protecting group. As a reference, one sample without the addition of an amino acid was carried through. After 24 hours the reactions were stopped and in stages 10 mL each of the solution were lyophilized.

The extraction of the product with ether was forgone, since the errors caused by potential impurities are inside the error margin of the functional experiment. Under the aspect that this experiment is dedicated to the assessment of adhesive interactions on a macroscopic level, this would seem plausible. The resulting products (PX) were stored at −20° C. The nomenclature is summarized in table 1.

TABLE 1

Nomenclature of the synthetized CMCs, PX; a) Mixture of PH, PC, PA and PK (15:20:30:35).

| Amino acid | DOPA | Lysine | Cysteine | Histidine | Mix[a] | — |
|---|---|---|---|---|---|---|
| Amino acid-CMC-hybrid | PA | PK | PC | PH | PHCAK | P0 |

The resulting amino acid-cellulose-hybrids were prepared as jellies, respectively. Additionally, a mixture of the modified CMCs of all of the four amino acids in a ratio of PH:PC:PA:PK 15:20:30:35 were used (PHCAK). These jellies were filled into a cell culture plate and submitted to a preliminary study regarding the required curing conditions.

Based on the results of the preliminary study, two bond strength studies for examining the adhesion to titanium were prepared. In study A, the pure jelly (P0) was joined with titanium under saltwater besides the catechol-containing jelly (PA) and the cysteine-modified jelly (PC) as well as the mixture PHCAKV. The saltwater solution was, after joining the samples, laced with $FeCl_3$ as oxidizing agent.

In study B, samples with the same jellies were joined. However, they were pre-treated (primed) with $FeCl_3$, i.e., the substrates were wetted with $FeCl_3$ solution and dried. Afterwards it was proceeded in an analogous manner to study A, however, without addition of $FeCl_3$ to the saltwater solution.

After four days of storage, the samples were tested, whereby the specimens of study B showed immediate adhesion malfunction.

The specimens of study A were evaluated with a bond tester in six-fold measurements. The mixture PHCAK showed similar adhesion strengths as the testing of the reference (ca. 2 N). PA showed a barely measureable adhesion (ca. 1 N). The adhesion samples that were joined with PC, lead to adhesion malfunction in all of the cases and did not survive the detachment from the joining device.

The fracture surfaces show an orange brown discoloration of the hardened jellies in all cases. This discoloration mainly appears close to the edges. Furthermore, large parts that were wetted with jelly, are not discolored and were present in a gel-like consistency. The samples that longest withstood the shear forces, show adhesive failure in large parts of the wetted region. Cohesive failures only appear occasionally (ca. 5%) close to the edges.

The premature adhesive failure of the PC samples can be explained by the lack of potential reaction partners such as catechols. Nevertheless, it remains open why these joinings as well as the ones of PA adhere worse than the reference.

The tested adhesive samples show clear evidence for the cause of the flexible joining in the fracture surfaces. Rigid regions can only be found close to the edges, which are in individual cases to be interpreted as witnesses of a cohesive failure. The red brown discoloration is caused by the complexed iron ions. The regions that are further away from the edge are still visibly present in the form of a gel. These areas thus do not contribute any cohesion to the bond strength.

This also expressed itself in the progression of the force-time diagram of the shear test (not shown). It could be derived from the parabola like function that it involved a non-hardened adhesive. This effect was also confirmed by Cha et al. [2]. They had expressed a mussel protein via bacteria and performed the posttranslational modification of the tyrosine in the flask. The adhesive joinings with unmodified proteins showed a similar parabola like progression.

Whereas the catechol containing samples (after posttranslational oxidation by tyrosinase) displayed the typical curve, in which a bond dissociation can be determined by a quick decrease of the force that acts against the applied shear force.

A more detailed view at the fracture surfaces reveals why these joining were not able to harden homogeneously. The hardening is, similar to the case of a polyurethane, diffusion controlled. From a critical thickness, in this case the distance from the edge, the hardening stops because of the absence of the required iron ions. This dependence of the hardening from complexation was examined strikingly in a corresponding experiment, the hydrogel study. Since in this case no joining parts restrict the jellies, the hardening progress could be documented photographically. The result of the sample for mixture PHCAK displayed the most homogeneous hardening process of all of the samples. The results of the corresponding storage of the gel pellets in saltwater that was laced with a $FeCl_3$ solution gave the most homogeneous hardening progress for the pellets of PHCAK as well as in study A regarding the bond strength.

[1] Leung, A. C. W.; Hrapovic, S.; Lam, E.; Liu, Y.; Male, K. B.; Mahmoud, K. A.; Luong, J. H. T. small 2011, 7, 302-305.

[2] Cha, H. J.; Hwang, D. S.; Lim, S.; White, J. D.; Matos-Perez, C. R.; Wilker, J. J. Biofouling 2009, 25, 99-107.

EXAMPLE 3

Application of a Gel-Forming System According to the Invention

An aditus to the lumen of the urinary tract (e.g., to the pelvicocaliceal system) is created either ureterorenoscopically (via the urethra, bladder or ureter) or percutaneously (via skin puncture at the flank). A specific port (a metal shaft if applicable) with an inner diameter of 3 to 9 mm is placed therein. An endoscope is inserted into the urinary tract lumen (e.g., into the pelvicocaliceal system) via the created aditus shaft, the surgical area is inspected and the urinary calculus or urinary calculi, respectively, is/are visualized. The urinary calculus or urinary calculi, respectively, is or are smashed by means of a holmium laser. The large and medium sized fragments are removed with the aid of a calculus catching instrument. 10 mL of a composition (B) according to example 1 are mixed with 1 mL of a composition (C) according to example 1 in a mixing syringe. Subsequently, a catheter is inserted via the endoscopy device (through the aditus) and the mixture of the compositions (B) and (C) is injected into the region of the urinary tract (e.g., into the pelvicocaliceal system) that contains the fragments of the smashed urinary calculus or calculi, respectively. The catheter is flushed with 0.9% NaCl solution and 10 mL (or more or less as required) of a composition (A) according to example 1 are applied, whereby the gel formation occurs over the course of approx. 1 min. Then a grasping instrument is inserted via the surgical endoscope via the aditus shaft. The solidified gel is grasped in one piece or in several parts with the grasping instrument and removed from the body via extraction.

The invention claimed is:

1. A method comprising:
fragmenting one or more urinary calculi in a region of a urinary tract so that a plurality of urinary calculus fragments are formed; and
after fragmenting, introducing composition (A) and composition (B) into the region of the urinary tract that contains the plurality of urinary calculus fragments,
wherein composition (A) comprises one or more cationically crosslinkable polymers,
wherein composition (B) comprises one or more crosslinking agents for crosslinking the one or more cationically crosslinkable polymers,
wherein in response to the composition (A) and the composition (B) coming into contact with each other and under conditions enabling crosslinking of the cationically crosslinkable polymers, a crosslinked gel is formed that partly or fully surrounds at least one urinary calculus fragment of the plurality of urinary calculus fragments, and
removing the at least one urinary calculus fragment with all of the crosslinked gel still partly or fully surrounding the at least one urinary calculus fragment.

2. The method according to claim 1, wherein the one or more of the cationically crosslinkable polymers of the composition (A) are selected from a group consisting of polyuronides, alginates, pectins and sodium carboxymethyl cellulose (CMC).

3. The method according to claim 1, wherein the one or more of the crosslinking agents of the composition (B) are selected from a group consisting of divalent cations and trivalent cations.

4. The method according to claim 1, wherein the composition (B) has an acidic pH-value in the range of 3.5 to 4.5.

5. The method according to claim 1, wherein
at least one of the composition (A) and the composition (B) includes magnetizable particles, and
the method further comprising introducing a composition (C) that contains magnetizable particles into the region of the urinary tract that contains at least one of urinary calculi and fragments of urinary calculi in a time delayed manner or at the same time with the composition (A) or the composition (B) so that the crosslinked gel additionally contains magnetizable particles.

6. The method according to claim 5, wherein the magnetizable particles are selected from particles comprising ferromagnetic elements.

7. The method according to claim 1, wherein one or more urinary calculi are one or more of kidney stones, urinary calculus fragments, kidney stone fragments, wherein the urinary tract is a kidney.

8. The method according to claim 1, wherein introducing composition (A) and composition (B) comprises introducing composition (B) before introducing composition (A).

9. The method according to claim 5, wherein the magnetizable particles are selected from particles comprising at least one of iron, nickel, cobalt, AlNiCo, SmCo, $Nd_2Fe_{14}B$, $Ni80Fe_{20}$, NiFeCo $Fe_3O_4$, and $\gamma$-$Fe_2O_3$.

* * * * *